United States Patent
Petel

(10) Patent No.: US 9,826,954 B2
(45) Date of Patent: Nov. 28, 2017

(54) DIAGNOSTIC FOR IN SITU DEFORMATION AND STRAIN MEASUREMENTS APPLICABLE TO TRAUMATIC INTERNAL INJURY INVESTIGATION AND PREVENTION

(71) Applicant: Oren E. Petel, Dollard des Ormeaux (CA)

(72) Inventor: Oren E. Petel, Dollard des Ormeaux (CA)

(*) Notice: Subject to any disclaimer, the term of this patent is extended or adjusted under 35 U.S.C. 154(b) by 206 days.

(21) Appl. No.: 14/614,258

(22) Filed: Feb. 4, 2015

(65) Prior Publication Data

US 2016/0220206 A1  Aug. 4, 2016

(51) Int. Cl.
*A61B 5/107* (2006.01)
*A61B 6/12* (2006.01)
(Continued)

(52) U.S. Cl.
CPC ............ *A61B 6/584* (2013.01); *A61B 5/1127* (2013.01); *A61B 5/1128* (2013.01); *A61B 6/50* (2013.01);
(Continued)

(58) Field of Classification Search
CPC .... A61B 6/00; A61B 6/12; A61B 6/50; A61B 6/501; A61B 6/58; A61B 6/583; A61B 6/584; A61B 5/00; A61B 5/03; A61B 5/031; A61B 5/103; A61B 5/107; A61B 5/1079; A61B 5/1126–5/1128; A61B 5/40; A61B 5/4058; A61B 5/4064; A61B 2560/00; A61B 2562/00; A61B 2562/04; A61B 2562/046; A61B 2562/16; A61B 2562/164; A61B 2576/00; A61B 2576/02; A61B 2576/026; G01T 1/00; G01T 1/16;
(Continued)

(56) References Cited

U.S. PATENT DOCUMENTS 5,524,636 A   6/1996 Sarvazyan
7,768,624 B2  8/2010 Cherala

FOREIGN PATENT DOCUMENTS

WO   WO 2012155137 A2 * 11/2012 ............. A61B 6/032

OTHER PUBLICATIONS

RM Wright and KT Ramesh, "An axonal strain injury criterion for traumatic brain injury," Biomechanics and Modelling in Mechanobiology, 2012, pp. 245-260, vol. 11.
(Continued)

*Primary Examiner* — Anastasia Midkiff

(57) ABSTRACT

A diagnostic gage (12) that can be implemented into a tissue-simulating headform (17) or other anthropomorphic surrogate test device (11) as a means of determining the internal strain within the test surrogate. One embodiment of the gage consists of a matrix or substrate embedded with x-ray contrast agents (14) and a series of holes within the substrate (15) that provide contrasting markers in an x-ray image and a means of closely coupling the gage to the test specimen. The relative motion of these contrasting markers can be monitored using x-ray fluoroscopy equipment (e.g., source (10) and detector (13)). This gage provides a means of determining the internal strain within a headform surrogate model for the purpose of evaluating the performance of helmets in terms of reducing the occurrence of concussion among other biomechanical injuries from trauma.

12 Claims, 9 Drawing Sheets

(51) Int. Cl.
*A61B 6/00* (2006.01)
*A61B 5/11* (2006.01)
*A42B 3/06* (2006.01)
*G01B 15/06* (2006.01)
*G01N 23/04* (2006.01)
*G09B 23/30* (2006.01)

(52) U.S. Cl.
CPC .............. *A61B 6/501* (2013.01); *A42B 3/06* (2013.01); *A61B 2562/164* (2013.01); *A61B 2576/026* (2013.01); *G01B 15/06* (2013.01); *G01N 23/04* (2013.01); *G09B 23/30* (2013.01)

(58) Field of Classification Search
CPC ....... G01T 1/29; G01T 1/2907; G01T 1/2914; G01T 1/2921; G01T 1/2928
See application file for complete search history.

(56) References Cited

OTHER PUBLICATIONS

RM Wright, A Post, B Hoshizaki, KT Ramesh, "A multiscale computational approach to estimating axonal damage under inertial loading of the head," Journal of Neurotrauma, 2013, pp. 102-118, vol. 30-2.
NJ Mills and A Gilchrist, "Oblique impact testing of bicycle helmets," International Journal of Impact Engineering, 2008, pp. 1075-1086, vol. 35.
U.S. Appl. No. 07/994,109, filed Jun. 11, 1996, A.P. Sarvazyan; A.R. Skovoroda.
U.S. Appl. No. 12/527,569, filed Jan. 21, 2010, I. Cunningham.
U.S. Appl. No. 11/695,469, filed Aug. 3, 2010, A. Cherala; S.V. Sreenivasan; B-J Choi.
U.S. Appl. No. 10/343,093, filed Oct. 2, 2003, A. Krstic.
U.S. Appl. No. 12/154,166, filed Nov. 27, 2008, G. Bertocci.
U.S. Appl. No. 12/819,824, filed Aug. 16, 2011, J. Cooper; M. Beebe; D.C. Stein; C. Morgan.
RG DePalma, DG Burris, HR Champion, and MJ Hodgson, "Blast Injuries", The New England Journal of Medicine, 2005, pp. 1335-1342, vol. 352.
American Society for Testing and Materials, "Standard Test Methods for Equipment and Procedures Used in Evaluating the Performance Characteristics of Protective Headgear", ASTM Standard F1446-06, 2006.
Biokinetics and Associates LTD., "Ballistic Load Sensing Headform", http://www.biokinetics.com/images/stories/products/bish/BLS_Headform_-_Brochure.pdf.
National Institute of Justice, "Ballistic Resistance of Body Armor", NIJ Standard-0101.06, 2008.
GT Desmoulin and JP Dionne, "Blast-Induced Neurotrauma: Surrogate Use, Loading Mechanisms and Cellular Responses," The Journal of Trauma, 2009, pp. 1113-1122, vol. 67-5.
EA Sogbesan, "Design and Analysis of Blast Induced Traumatic Brain Injury Mechanism Using a Surrogate Headform: Instrumentation and Outcomes," Master of Engineering Thesis, University of Nebraska, 2011.
A Bouamoul, K Williams, and JS Binette, "Development of a Biofidelic Headform for mTBI Assessment", 3rd Personal Protective Equipment Conference, 2010.
L. Cannon, "Behind Armour Blunt Trauma—an emerging problem". Journal of the Royal Army Medical Corps, 2001, pp. 87-95, vol. 147.
HLA Van Den Bosch, "Crash Helmet Testing and Design Specifications," University Press Facilities, Eindhoven, The Netherlands, 2006, 155 pages.
Biokinetics and Associates LTD., "Blunt Trauma Torso Rig", http://www.biokinetics.com/images/stories/products/bttr/BTT_Rig_-_Brochure.pdf.
PA Taylor, JS Ludwigsen, and CC Ford, "Investigation of blast-induced traumatic brain injury", Brain Injury, 2014. Pages 879-895, vol. 28-7.
KE Simmonds, P Matic, M Chase, and A Leung, "GelMan: A Physical Model for Measuring the Response to Blast" http://www.nri.navy.mil/research/nrl-review/2004/materials-science/almmonds/.
H Zou, JP Schmiedeler, WN Hardy, "Separating brain motion Into rigid body displacement and deformation under low-severity impacts" Journal of Biomechanics, 2007, pp. 1183-1191, vol. 40.
TC Chu, WF Ranson, MA Sutton, and WH Peters, "Applications of digital-image-correlation techniques to experimental mechanics" Experimental Mechanics. 1985, pp. 232-244, vol. 25.
BK Bay, "Methods and applications of digital volume correlation," Journal of Strain Analysis for Engineering Design, 2000, pp. 745-760, vol. 43.

\* cited by examiner

DIAGNOSTIC FOR IN SITU DEFORMATION AND STRAIN MEASUREMENTS APPLICABLE TO TRAUMATIC INTERNAL INJURY INVESTIGATION AND PREVENTION

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

Field

This application relates to a diagnostic gage designed to measure the internal deformation and strain history within soft-tissue anthropomorphic test devices as a means of evaluating the potential for an internal injuries from an external traumatic force application.

Prior Art

Internal traumatic injuries can result from various types of impacts, including scenarios in which the impacts do not result in a penetration of a person's body. Examples of such internal traumatic injuries that do not involve penetration are concussions as well as other head injuries within the traumatic brain injury spectrum and blunt impact trauma. Being in close proximity to an explosion can similarly result in internal traumatic injuries from blast wave exposure, targeting specific organs such as the lungs and brain, among others (DePalma et al., 2005). While protective equipment is often worn by those at risk of suffering these injuries, such as professional and amateur athletes, military personnel, as well as police forces and other security personnel, the prevalence of these types of injuries remains high despite contemporary certification standards. The development of new tools that can be used in the design and certification of protective equipment would help to further the development of protective equipment, reducing the prevalence of these injuries.

The current standards for the certification and design of protective equipment rely on combinations of diagnostic systems such as: accelerometers (ASTM Standard F1446-06, 2006), load-cell measurements (Biokinetics and Associates LTD), pressure transducers, and backface indentation measurements in clay (NU Standard-0101.06, 2008). The choice of diagnostic is specific to the type of protective equipment that is being designed and certified. All of these measurement techniques have drawbacks that limit their ability to accurately predict injury levels. Materials, including bio-materials are particularly sensitive to strain failure (Wright and Ramesh, 2011), however none of the current diagnostics used in dynamic injury prediction are able to measure the dynamic strains in soft materials. These shortcomings will be discussed in further detail for specific testing procedures used to investigate injury prevention and safety equipment certification.

Impact Testing of Helmets with Anthropomorphic Headforms

Certification of protective helmets under impact loading currently uses anthropomorphic test devices (ATD), such as the Hybrid III crash test dummy, with one or more of the aforementioned diagnostic systems that are able to measure the rigid body mechanics of the ATDs. In accordance with the standards of the American Society for Testing and Materials (ASTM), helmet certification involves drop testing of a hollow metal headform that is fitted with the helmet being tested. The acceleration/deceleration of the head is measured and correlated to expected injury thresholds (Desmoulin and Dionne, 2009), measurements that focus on the rigid body mechanics of the headform.

As the headform consists of a hollow metal construction, these tests are unable to include metrics related to the expected internal deformation of the skull and/or brain that would be suffered by a helmet wearer. Similarly, any deformation of the headform itself is unrelated to the skull deformation that would be experienced by a helmet wearer under these impact conditions since the mechanical properties of the headform material (aluminum) differs from that of the human skull.

The shortcomings of the headforms currently being used in helmet certification testing have led to the development of several novel headforms that contain materials intended to simulate biological tissues, such as the skull and brain, relying on a combination of polymers and elastomers (Sogbesan, 2011; Bouamoul et al., 2010). These headforms have anthropomorphic features with a high degree of bio-fidelity. Nevertheless, the diagnostics integrated into these headforms consist of localized single-point measurements using either pressure transducers or accelerometers that greatly depend on the chosen location at which the diagnostics are placed. While point measurements are sufficient to study the rigid body mechanics of an impact, such as the response of a hollow metal headform, a full-field measurement diagnostic is necessary to capture the deformation that occurs in the soft-tissue headforms under development. The vast majority of materials will fail due to high levels of shear, however none of the available diagnostic systems are able to measure shear, limiting their ability to predict the material or structural failure that might occur in biological tissues under impact loading.

Internal Markers Used in Head Injury Assessment

An experimental technique has been developed based on bi-planar x-ray tracking of a large number of dispersed neutral density markers that were inserted in a cadaver brain (Zou et al., 2001). These markers were used to track the bulk motion of various parts of the brain as the head was subjected to low-speed impacts and rapid acceleration/deceleration events; however, a limited number of markers were used in the measurement resulted in a spatial resolution that was insufficient for a dynamic strain measurement within the cranium. Similar investigations were undertaken by van den Bosch (2006), however the investigation involved a soft-tissue headform rather than a cadaver brain. Neither of these nor subsequent investigations by the same researchers attempted to measure the shear or normal strains within the brain, focusing primarily on the motion of the brain. These shortcomings mean that identifying locations of probable injury based on these motions is limited to the peripheral boundaries of the brain, since the internal strain field is not known. Knowledge of the internal strain field could identify internal areas affected by an impact of acceleration/deceleration event.

Blunt and Ballistic Impact Testing with Protective Equipment

There are a wide variety of blunt impacts that can cause internal injuries even when protective equipment is worn. Some examples of non-penetrating blunt impact injuries include behind armor blunt trauma resulting from a ballistic impact on body armor (Cannon, 2001). Similarly, stab and blunt weapon impact can also cause behind armor injuries, although these are often less severe.

Currently, the standard measure of acceptable behind armor deformation is provided by the guidelines of the National institute of Justice standard (NU Standard-0101.06, 2008). In this certification methodology, the armor is backed by plastilina clay, the depth of clay penetration is measured following each ballistic impact experiment and the depths are used to classify the performance of the armors. The clay that is used in this certification is not characterized as a bio-simulating material and measurements of the deformation are not made in real-time during the impact, but as a post-impact analysis. This technique is meant to capture the peak deformation of the armor, however recent investigations have shown that the clay quickly decouples from the backface of the armor, leading to concerns of inherent inconsistencies in experimental results.

Some dynamic testing systems are currently in use to determine levels of behind armor blunt trauma. One example is the Blunt Trauma Torso Rig (Biokinetics and Associates Ltd.), which measures the displacement of a flexible membrane that is correlated to chest wall behavior. However, chest wall velocities do not directly indicate the stress or strain level that results inside the chest, making a correlation between this membrane velocity and injury tenuous. Measurements of the internal shear stresses and strains would provide superior insight into the injury mechanics involved in these trauma events, providing a direct measurement of the internal dynamic deformation.

Traumatic Brain Injury from Blast Wave and Head Impacts

With the prevalence of non-penetrating traumatic battlefield injuries, such as traumatic brain injury (TBI), among personnel returning from active duty, there has been an increase in research focused on the dynamics that lead to these injuries. In efforts to understand the biological response to trauma from either impact or blast waves, many researchers have focused on inserting miniature pressure transducers into animals as well as soft-tissue simulating anthropomorphic headforms, for experimentation (Desmoulin and Dionne, 2009). These measurements return time-resolved pressure histories, limited to discrete locations chosen by the researchers. The nature of a single point, localized measurement is a significant technical deficiency in that locations of peak stress could exist in regions adjacent to the measurement.

While injury can be shown to scale with pressure, measuring a localized mean stress within the body could be misleading as a predictor of injury since materials, including biomaterials, typically fail under shear, which is not measured. Furthermore, shear stresses and strains cannot be reliably calculated from localized pressure measurements as the complex loading environment does not allow for this simple calculation. Numerical simulations of a blast wave interacting with a detailed model of a human cranium have shown that significant shear stresses and strains are likely to develop within areas of the brain due to the wave interactions and material properties of the tissue (Taylor and Ford, 2009). However, shear stresses and strains are not easily measurable with physical gages in this complex loading scenario, and require a novel diagnostic approach that can measure full-field dynamic strain within headforms.

Blast Wave Internal Injury Characterization

Similar localized pressure measurements are used for investigations into primary blast injuries, which target specific internal organs. Several tissue-simulating anthropomorphic test dummies, such as GelMan (Simmons et al.), have been developed for the purpose of identifying these internal injuries and the safety thresholds for the design of protective equipment. The use of a full-field strain measurement technology, rather than localized point measurements would greatly enhance the injury prevention capabilities of these internal injury test devices.

SUMMARY OF INVENTION

In light of the state of prior art in the field of internal injury biomechanics, it can be appreciated that there exists a need for a novel technology that allows for full-field, time-resolved strain (deformation) measurement integrated in tissue-simulating anthropomorphic test devices (ATD), which is one embodiment of the invention. The limitations of the current testing and certification methods related to protective equipment designed to protect against internal traumatic injuries, particularly head injuries, is evident from the prevalence of such injuries. Internal deformation metrics from tissue-simulating materials integrated into testing devices are necessary to redesign helmets as well as other protective equipment to provide superior protection.

The present invention is a genre of gage that is (in its primary embodiment) a tool for measuring the deformation of soft tissue or soft tissue-simulants under an arbitrary loading condition. The gage consists of a substrate integrated or coated with x-ray contrast agents that can be introduced into the tissue-simulants of an ATD, headform, or within a biological system itself along an internal surface or plane in which the deformation is to be measured. The gage is monitored using fluoroscopic techniques (multiple x-ray images or x-ray videography) to determine the time-resolved motion of the contrast materials. It is important that the contract material is integrated in a manner that does not significantly impede the deformation of the tissue-simulant being measured, while adequately coupling the motion of the tissue-simulant to the contrast agents. The contrast material must be integrated such that there are variations in x-ray absorption that would produce a series of spots or speckles when imaged with a given fluoroscopic system. Taking multiple images with the fluoroscopic configuration, the relative motion of these distinct spots between successive images and the deformation history within the tissue-simulants can be obtained through existing speckle correlation algorithms. Thus, the gage can be used to determine regions within the test specimen (ATD) of high deformation/strain that can be directly linked to possible injury outcomes. Use of the gage to measure internal strain histories in tissue-simulants within ATDs and headforms will increase the reliability of the predictions of injury outcomes and provide a diagnostic that can improve the certification standards for personal protective equipment, replacing the unreliable accelerometer-based methods currently employed.

Continuous or multi-anode x-ray sources can be used to image the ATD and associated contrast agent. The time resolution of the deformation history is provided by the use of one or many high-speed cameras, photodiodes, or similar optical detectors coupled to fluoroscopic screens (scintillator materials or phosphors) to record the relative locations of the contrast agents. To ensure sufficient time resolution, the fluoroscopic screens should involve coupling scintillating materials and phosphors with appropriate decay times to allow for high-speed imaging. It may be necessary to use image intensifiers between the scintillator and optical detector. Similarly, collimating the x-ray beams either before the target specimen (ATD) or before the scintillator screen could be necessary to increase spatial resolution of the final images. There should be a camera and fluoroscopic screen for every x-ray source involved in the imaging process.

A single source-detector configuration can be used to make two-dimensional strain measurements, however multiple sources and detectors can be used to generate three-dimensional strain measurements. Care must be taken to calibrate the fluoroscopic configuration for the skewing of the image resulting from possible x-ray image distortions. When the contrast materials are introduced on a curved or textured surface, using multiple sources and detectors for the investigation is desirable, although it is still possible to use a single detector if care is taken in the analysis of the deformation results.

The terms contrast agent, contrast material(s), and contrast markers will be used interchangeably throughout this document.

DRAWINGS—REFERENCE NUMERALS

Figure 3:
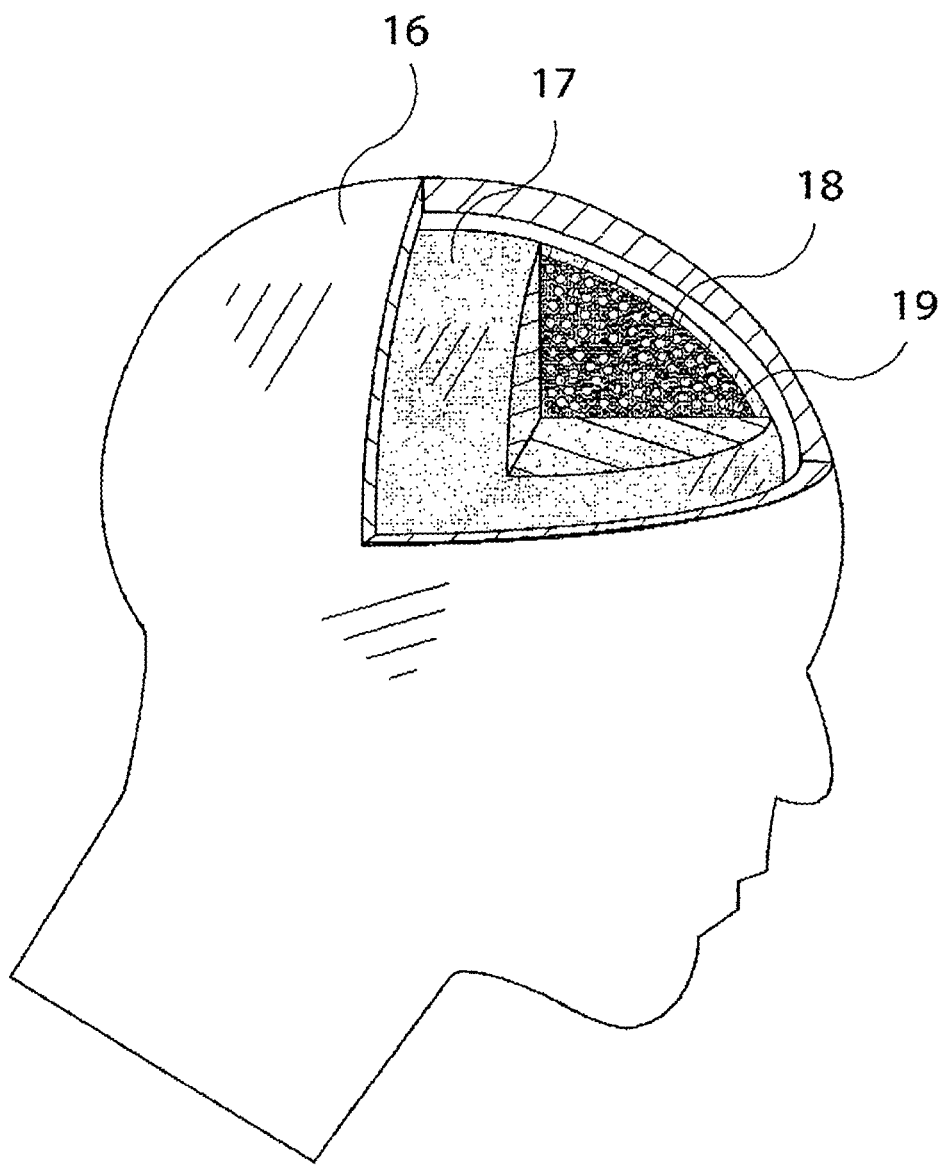
FIG. 3 shows the integration of a scaffolding gage embodiment (of the type shown in FIG. 2) integrated into a soft-tissue simulating ATD headform for the evaluation of internal deformation relating to head trauma. For clarity, the headform s sectioned (cutaway diagram) to illustrate internal features and one possible location for gage placement.

10—X-ray tube/source
11—Anthropomorphic Test Device (ATD), also called the test specimen, to be investigated for deformation
12—An embodiment of the gage that is embedded in an ATD or target material of interest.
13—Fluoroscopic detector
14—Polymeric, elastomeric or other material substrate that is mixed with a finely integrated x-ray contrast agent during the substrate preparation.
15—Holes in the mixed substrate/contrast agent which enable intimate integrating of the gage into a cast or grown target specimen (e.g., ATD), acting as a scaffold as well as a source of x-ray attenuation contrast.
16—Outer layer of a soft-tissue simulating anthropomorphic headform.
17—Anthropomorphic brain simulator with soft-tissue simulant contained within the headform.
18—Embodiment of the gage with a scaffolding-type design that is cast within the brain-simulating tissues.
19—Holes within the scaffolding-type gage that couple the gage to the tissue-simulant and provide contrast.
20—Drop tower arm.
21—Soft-tissue headform with integrated gage embodiment (as represented in FIG. 3).
22—Helmet being tested.
23—Fluoroscopic detector system (x-ray tube/source not seen since the figure is drawn from the vantage point of the x-ray source). This could be a scintillator screen optically coupled to a high speed video camera through objective and relay lenses involving an Image intensifier. Or alternatively it could be a x-ray image intensifier optically coupled to a high-speed video camera.
24—Impact Anvil.
25—Polymeric, elastomeric or other material substrate.
26—Contrast agent.
27—Polymeric, elastomeric or other material substrate.
28—Particles of the contrast agent embedded in a substrate.
29—Shell or cover (e.g., a helmet) of a material specimen of interest.
30—Internal surface within a shell or cover that prevents direct visual verification of the surface or internal plane behavior.
31—Contrast agent.
32—Polymeric, elastomeric, tissue or tissue-simulating material substrate.
33—Contrast agent.
34—Hole in a scaffolding-type gage that can accommodate anthropomorphic features, such as tissue-simulating models of organs or bones in an ATD.
35—Tissue-simulating ATD of a torso to investigate blunt impact trauma.
36—Deformation gage embedded in a blunt trauma test device of an anthropomorphic torso in a manner that can accommodate anthropomorphic features, such as organs or bones.

39—Protective armor plate or fabrics.
40—Bullet or impactor.

Detailed Description—First Embodiment—FIGS. (1-3)

In its first embodiment, the gage 12 is introduced into an Internal plane of the test material 11 (e.g., anthropomorphic soft-tissue simulating headform) that is to be loaded with any type of force and its deformation is investigated (FIG. 1) using radiographic videography techniques (e.g., x-ray videography or fluoroscopy). In its first embodiment, the gage consists of a contrast agent that is mixed into a substrate material 14 at a considerably fine scale (e.g., as a powder) with a volume fraction of at least 5% contrast agent. The substrate material could be any polymeric, elastomeric or other material that can be prepared as it is being mixed with the contrast agent to allow casting of the gage with a series of holes 15 as shown in FIG. 2.

The holes 15 in the gage, the size of which will depend on the magnification and resolution of the imaging configuration, must be large enough to encompass at least 4 pixels on the digital receiver, with an equivalent average minimal spacing between subsequent holes. These holes have two functions. (i) The first function of the holes 15 is to provide a contrast in x-ray absorption to the contrast-agent containing substrate 14. The size of the holes will depend on the spatial resolution of the detector being used to ensure adequate resolution of the resulting images. (ii) The second function of the holes 15 is to provide a scaffold that will be used to cast the gage into the test material (e.g., headform ATD). For example, if the gage were to be placed into a headform 16, the gage would likely be placed into a tissue-simulating material that models the human brain. During the casting or moulding process to create this brain-simulating component 17, the gage 18 can be placed in the appropriate location within the mould and the elastomer used to mimic brain tissues would be made to penetrate through the holes 19 in the gages. This would ensure an intimate coupling of the gage 18 into the material being tested, where the gage 18 could be used as a casting scaffold. This type of integration is demonstrated in the sectioned schematic of a headform with embedded gauge in FIG. 3.

The primary component of the gage in the present embodiment (i.e., the substrate) should ideally be made of the same material as the tissue simulant. For example, if the brain-simulating component 17 is prepared from a siloxane elastomer, it is preferable that the same siloxane elastomer be mixed with the contrast agent to prepare the scaffolding-type gage 18. This would ensure a close match in density and acoustic impedance of the gage to the material it is being used to probe and thus dose dynamic coupling during deformation. If it is not possible to use the same materials for both the gage and target material specimen, care should be taken to closely match the density and acoustic impedance of the gage to the materials being tested to ensure an appropriate coupling of the gage 11 to the tested specimen 17.

The contrast agent could be any high atomic number material that is introduced into the ATD for imaging purposes. The choice of contrast agent should aim to match the density of the material into which it is to be integrated as closely as possible. While metal powders, such as Lead (Pb), are an obvious choice for their high atomic number, they typically have high bulk densities and acoustic impedances that do not closely match those of the elastomers and polymers. The present embodiment favours alternate contrast agents. Examples of contrast agents that provide low density and high atomic number possibilities consist primarily of phosphors and salts, among other materials. Some of these materials could be considerably reactive and care should be taken to ensure the safety and compatibility of integrating them into the chosen tissue-simulant or materials. Current designs and prototypes favor the use of Potassium Iodide (KI), which is an example of a low-density material with low reactivity that has a relatively high atomic number and proves to be a decent contrast agent. There exist numerous materials that could be used as radiocontrast agents for this application, such as Barium Sulfate ($BaSO_4$), which is commonly used in medical applications. Potassium Iodide is favored over Barium Sulfate for this application at this time due to its lower density. Current designs of the first embodiment favor a gage thickness that is about 1 mm thick, while the holes size will scale based on several design constraints (e.g., lengthscales and area of interest, desired spatial resolution, casting limitations, and the x-ray magnification factor). The schematics of the embodiment were purposefully scaled to emphasize the features of the gage and do not represent the scale at which the embodiment is necessarily intended for use. The contrast agent and hole pattern should be designed in a manner that produces numerous well-defined and randomly distributed high-contrast ratio speckles or markers within the ATD when imaged with an x-ray source 10 and fluoroscopic imaging device 13.

During the molding or casting process, the polymer will be made to penetrate into the aforementioned holes in the scaffolding contrast layer, allowing for direct motion coupling between the scaffolding contrast layer and the elastomer in terms of their deformation history. The contrast in the x-ray images will be provided by the difference in the x-ray attenuation within the mixed scaffolding contrast layer and the polymer-filled holes. The motion of the filled holes can be tracked and used to determine the deformation history of the test specimen (e.g., ATD headform).

Operation of the First Embodiment—FIGS. (1-4)

Figure 1:
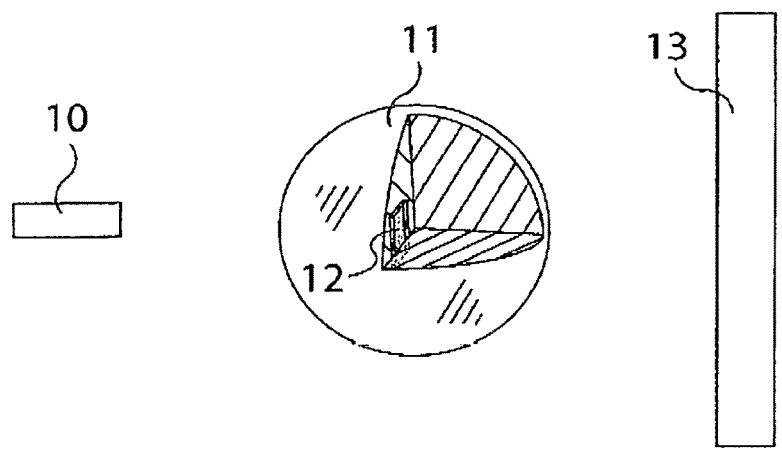
FIG. 1 shows one of several possible configurations of the x-ray tube source, fluoroscopic detector, and target specimen (ATD is represented by a sphere and it is configured with an embedded gage) that can be used to measure the dynamic deformation of the ATD using an embedded embodiment of the gage. Note that the target specimen is a cutaway diagram to show its internal features, which includes the embedded gage.
Figure 2:
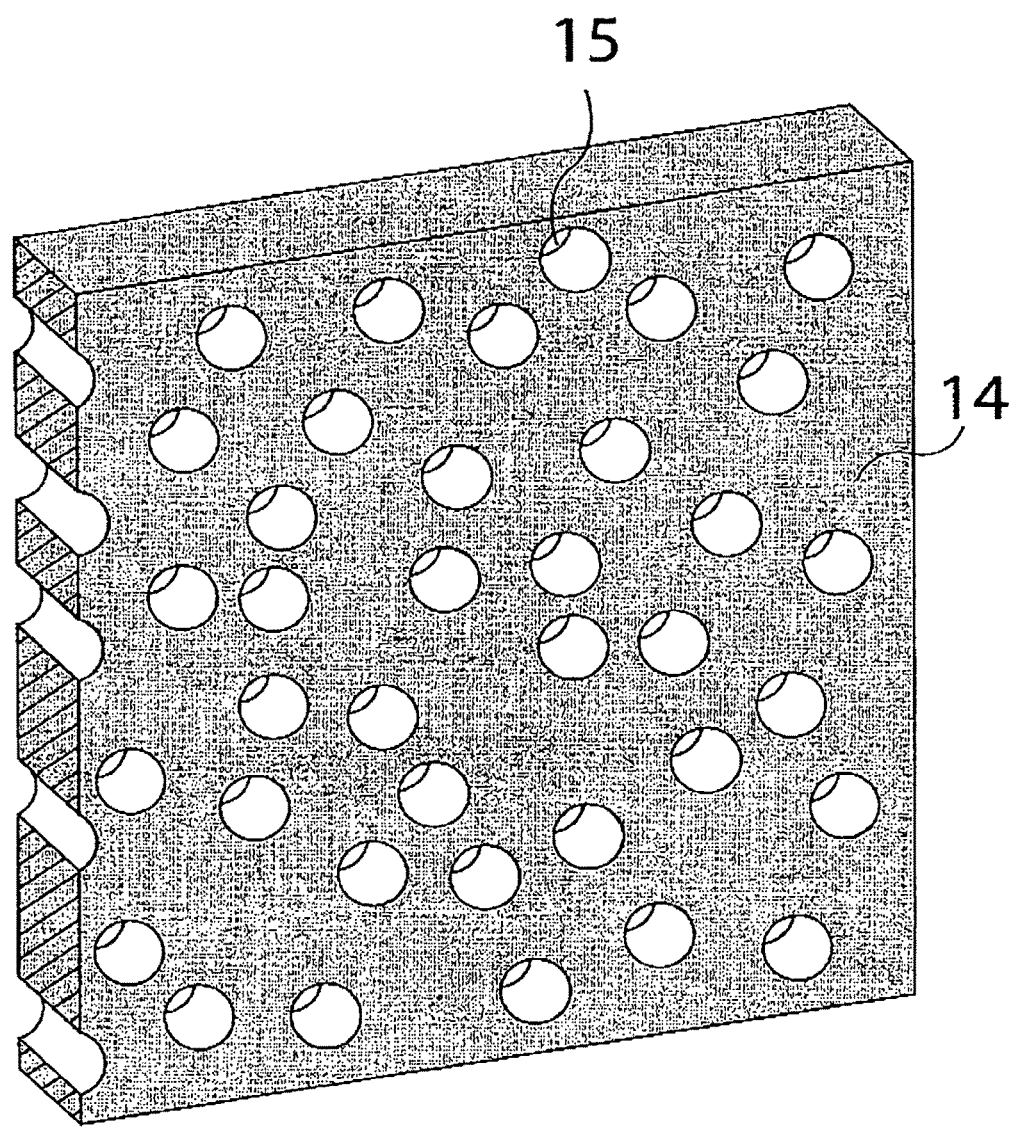
FIG. 2 shows an embodiment of the gage in which the contrast agent is finely mixed within an elastomer, polymer or other material and molded into a scaffolding type substrate around with the target specimen can be build or cast.

As illustrated in FIG. 1, the gage 12 must be placed within a test specimen 11 that is situated between an x-ray source 10 and detector 13. The test specimen can be any material that results in less attenuation of the x-ray beam than the contrast agent. For many applications, particularly those analysing the performance of protective equipment, hard x-ray sources are more suitable than soft x-ray sources due to the superior penetrating lengths of hard x-rays, which should allow for superior discretion between surrounding materials and the contrast agents. The current embodiment favours continuous x-ray sources that operate with a peak voltage of approximately 150 kV, although multi-anode sources as wen as higher energy x-ray sources could also be used for x-ray videography purposes.

There are two possible configurations of the source and detector that are currently favored, each with their own advantages, depending on the application. The first involves a large flat-panel scintillator, optically coupled to an image intensifier that is optically coupled to an ultra-high-speed camera or sensor array. To obtain superior spatial resolution for the detector imaging system, columnar-type crystal scintillator panels should be used. The crystal columns can be prepared with minimum characteristic widths (or diameters) of 10-60 μm within panel sizes on the order of 50 cm×50 cm to allow for imaging of larger ATD components. By decoupling the optical and scintillation components, the spatial resolution of the detection setup can be increased with reduced distortion of the images, although care must be taken to ensure that there is sufficient photon production by the scintillator to support this setup. An alternate construction of the x-ray detection system would involve the use of commercial x-ray image intensifiers, such as the Thales TH9447QX models with a sufficiently quick decaying output phosphor. For some impact applications, these x-ray image intensifiers may not contain output phosphors with sufficient decay times and the use of decay-weighted image subtraction techniques during image processing may increase the effective framing rates of the detection system.

The gage described in the preceding section (FIG. 2) is intended to be integrated intimately into the mid-plane of a cast (or assembled) specimen material or interest, which could be a soft-tissue surrogate or similar specimen. A schematic of one possible type of integration of the gage 18 into a soft-tissue simulating headform 16 is shown in FIG. 3. The test specimen containing the gage 18 should be placed between the x-ray source 10 and the time-resolved x-ray fluoroscopic detection equipment 13 (see FIG. 1). The test specimen can be subjected to any type of loading condition, an example of which is a drop tower test 20 in which an ATD headform 21 (i.e., the test specimen) is fitted with a helmet 22 to investigate the deformation pattern within the soft-tissue surrogate resulting from an impact onto an anvil 24 to assess the helmet effectiveness (see FIG. 4). The force applied to the gage will result in a relative motion of the holes 15/19 in the gage 14/18 (i.e., contrasted regions in the image). By monitoring the relative displacement history of the features (speckles/markers) of the gage under loading, the locations of the features can be cross-correlated in a manner that provides a quantitative measurement of the internal deformation (strain) within the gage and by extension the specimen (ATD) being tested. The algorithms related to Digital Image Correlation (Chu et al., 1985) would apply to determining the strain history in the material. One of the main benefits of this measurement and data processing approach is that the data obtained is resolved over an entire plane rather than at a single point, as would result from using a strain gage; thus, it is less dependent on gage placement.

The internal deformation history, generated by an appropriate image correlation algorithm, of the tissue-simulating ATD can then be correlated to a sustained injury. The contrast agent can be placed along a mid-plane, curved internal surface or several planes and surfaces within the ATD that are at risk of large internal deformation, and thus injury within the human body. The primary advantage of the invention over the prior art in the field s the ability to measure the full-field strain within any region of the ATD as well as ability to measure the shear strains that develop within the ATD, predictors of injury in biological tissues (Wright and Ramesh, 2011; Wright et al., 2013). Currently, diagnostic systems that can provide dynamic measurements of principal and shear strain in dynamically loaded biological tissues or tissue stimulants are not available.

It is recommended to calibrate the Image on the fluoroscopic detector 23 using a known calibration template to ensure proper magnification and resolution prior to impacting the actual specimen. This calibration process will also enable the operator to determine the level of distortion in the x-ray image produced by the x-ray tube and detector assembly. Image processing will be necessary to adjust the contrast marker locations based on the inherent distortions due to the imaging configuration. In order to increase the temporal resolution of the gages during operation, a phosphor decay constant-weighted image subtraction algorithm could be implemented, which would be particularly effective for the gages described in this document. The specimen should also be fitted with fiducial markers to calibrate the magnification seen in a given fluoroscopic configuration.

Detailed Description of Other Embodiments—FIGS. (5-9)

Other embodiments of the gage will be described based on various methods of integrating the contrast agent into the gages. The operation of the gage in any of its embodiments is relatively similar in the manner in which the deformation history of the gage can be obtained. The loading techniques used to deform the test specimens, one example of which is drop test shown in FIG. 4, can be varied for the loading purposes desired.

Contrast Agent Integration Methods

The contrast agent must be introduced in sufficient quantity to provide contrast to the image of the ATD and provide a reasonable pattern for the image processing of the deformation field while not interfering with the deformation of the ATD that is being measured. Assuming that a castable elastomer is used as the tissue-simulant in the ATD, there are a number of Integration methods for the contrast agent into a test specimen than that described in the first embodiment of the gage.

Coated Contrast Materials on and into Substrate Layers

Figure 5:
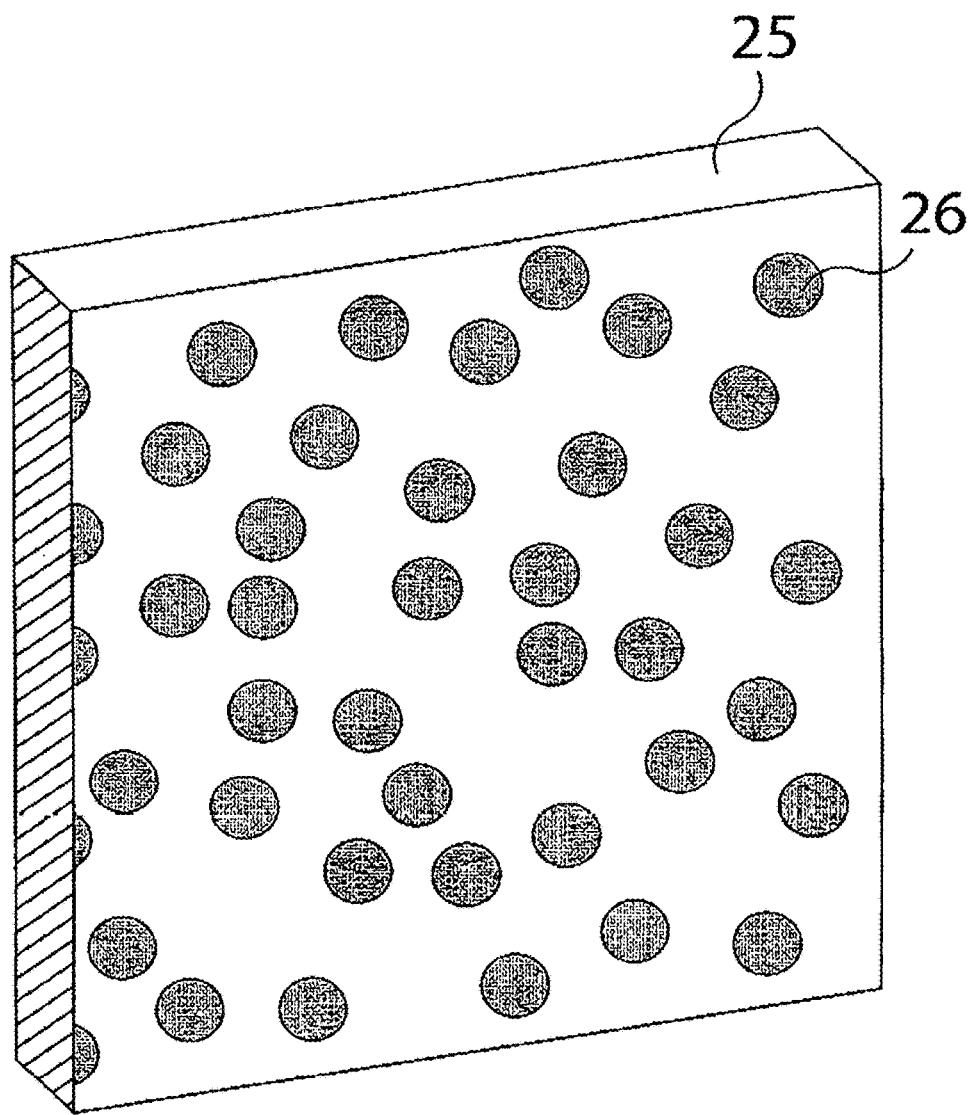
FIG. 5 shows another embodiment of the gage in which the contrast agent is coated or placed onto the surface of a polymeric, elastomeric or other substrate in a randomized pattern.
Figure 6:
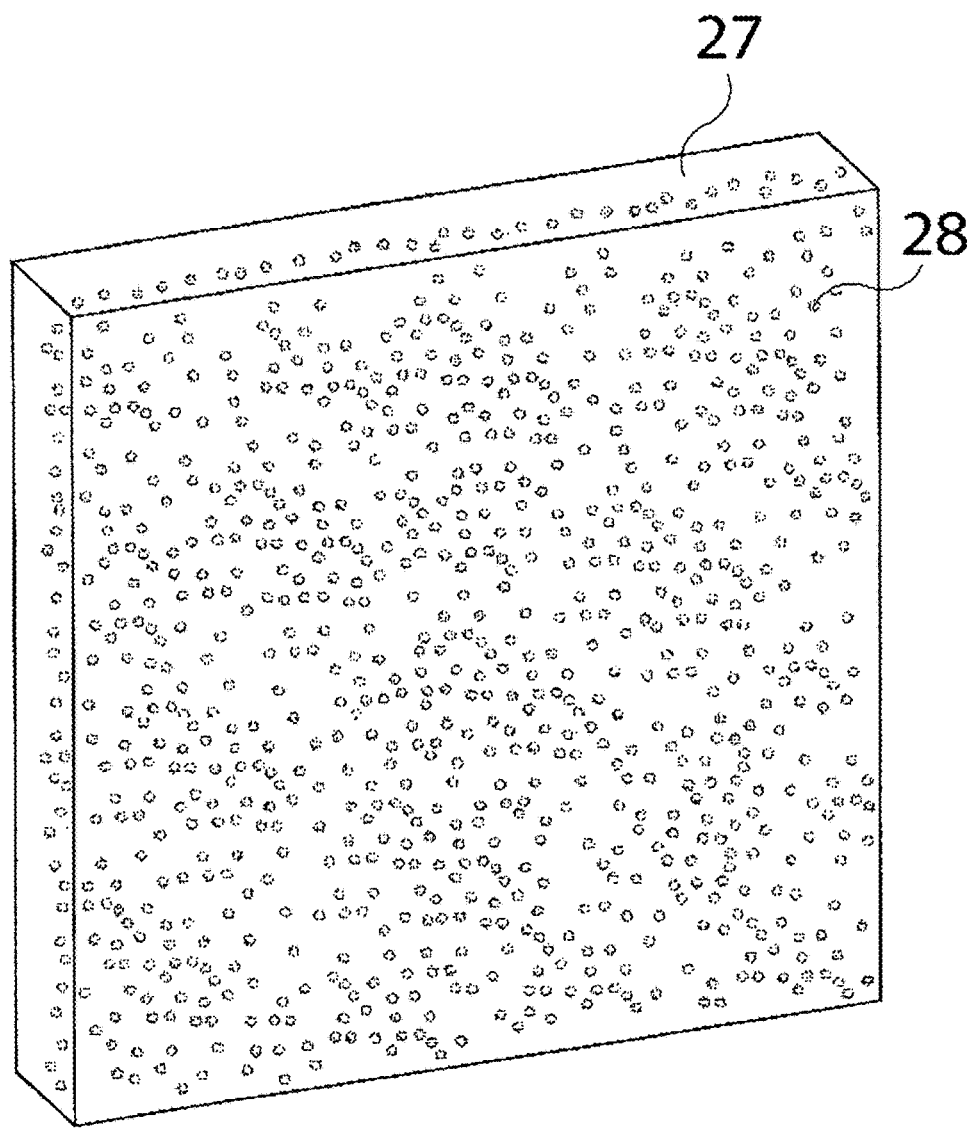
FIG. 6 shows an embodiment of the gage in which the contrast agent consists of individual particles cast within a polymeric, elastomeric, or other substrate.

Contrast layers can be introduced as films that are cast into the mid-planes of the soft tissue-simulants of an ATD. The contrast layers can consist of elastomeric or polymeric substrates 25 onto which a contrast agent 26 can be introduced (FIG. 5). The contrast agent 26 can be introduced onto the substrate through deposition, sprinkled in particle form onto a curing surface, or mixed into a resin or paint that can be cured on the surface of the substrate 25, among other coating techniques. The contrast agent must be applied in a manner (thickness and geometry) that produces a pattern with sufficient contrast to the x-rays. The contrast materials 28 could similarly be integrated as discrete particles deposited through various means into the substrate layer 27 (FIG. 6).

Figure 7:
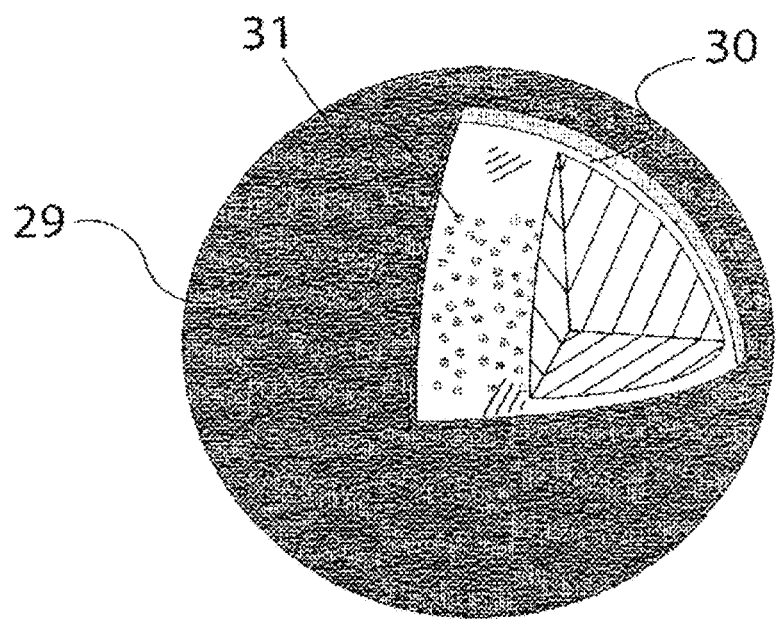
FIG. 7 shows a three-dimensional view of a multi-layered target specimen, whereby the contrast agent is applied to a curved or textured surface on an internal plane that is contained within an outer shell or cover.

The substrate can be planar or curved depending on the desired measurement location and the number of x-ray sources being used. The substrate is then integrated during the moulding process of the desired testing specimen (e.g., ATD part). For example, if the ATD is to include a biofidelic brain surrogate made from tissue-simulants, the substrate could be placed in the sagittal, coronal or any other plane during casting. If the desired measurement location is on the outer surface of a specimen that is contained within an outer shell 29, the gage could be prepared as a thin film 31, which is then adhered to the outer surface of the specimen 30 (e.g., the outer region of a headform that is contained under a helmet). This is demonstrated schematically in FIG. 7, where the contrast agent could be introduced as a thin film 31 overlaying the part or directly deposited onto the internal specimen 30.

Other Uses and Methods Involving Scaffolding-Type Layers

Figure 8:
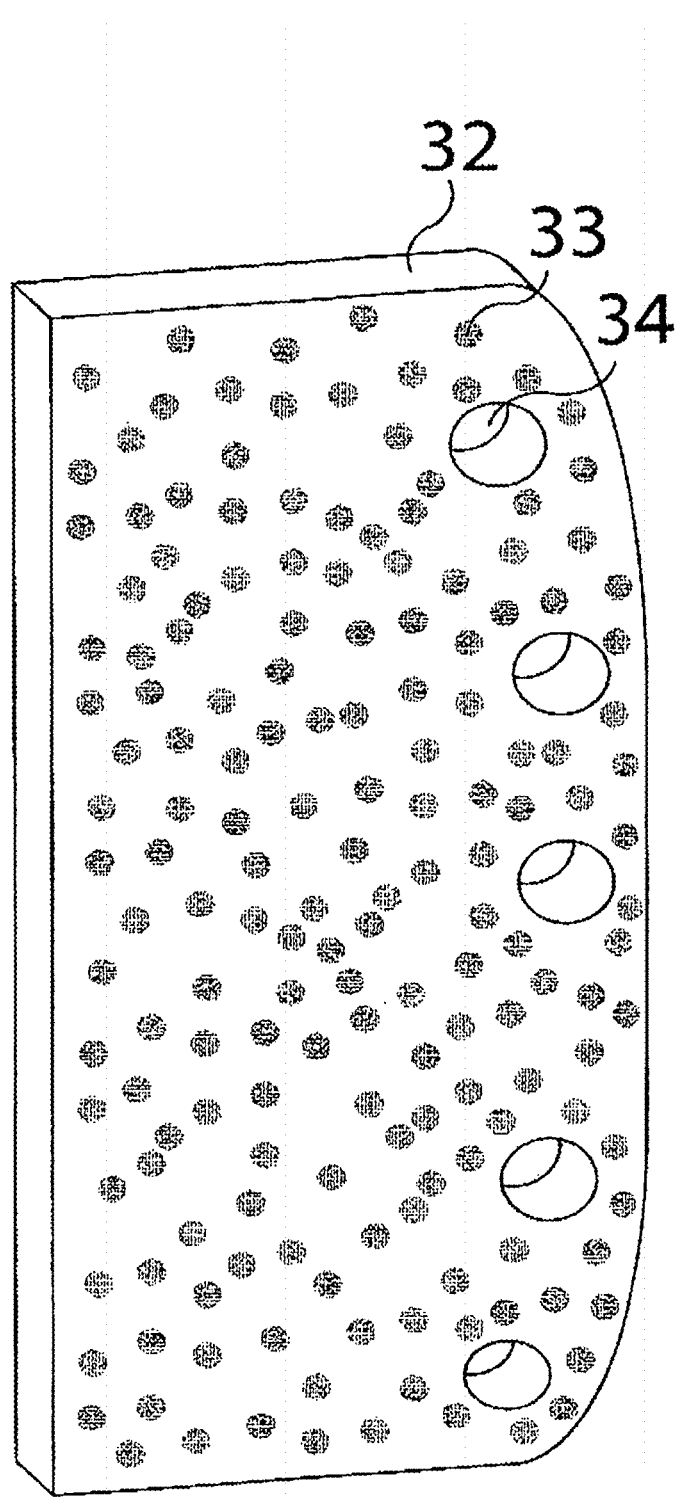
FIG. 8 shows an embodiment in which a scaffolding substrate is coated or embedded with contrast materials. As opposed to the embodiment in FIG. 2, the holes are not used for contrast purposes, they are only used as scaffolds for casting the substrate based gage into a target specimen.

One example of introducing the contrast agent involves moulding a contrast layer that can be used as a scaffold during the casting of the ATD features, such as an elastomeric brain with bio-fidelity as described in the first embodiment of the gage. The mould that is used to cast the layer should be contoured to match the ATD or test specimen, including internal features (e.g., a rib cage in the case of a torso model, see FIG. 8 and FIG. 9) as well as having randomly spaced parts that generate holes 34 in the scaffolding contrast layer 32/33. The gage 36 with contrast markers will behave as a scaffold around which the main biofidelic body part model 35 is cast.

A possible future use of this first embodiment of the gage would be to generate a scaffolding-type gage onto which biological tissues can be grown; although, it should be noted that the technology and associated resource costs makes it not a viable approach at the this time.

Select Applications of the Invention

Head Impact—Helmet Performance Evaluation

Figure 4:
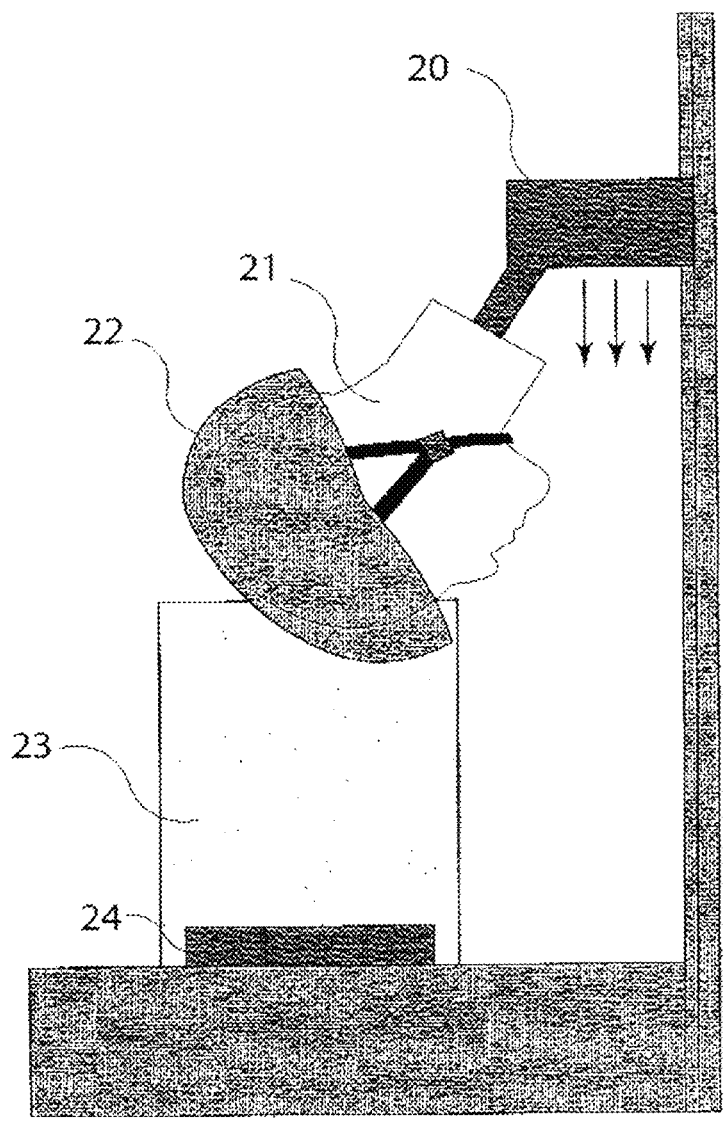
FIG. 4 shows an example of the type of testing that can be carried out using the gage embodiments integrated into a ATD headform (from FIG. 3) to test the effectiveness of a helmet at reducing the internal deformation (internal trauma) of the brain-simulant during a blunt impact event. The helmet is drawn as a transparent part to show the placement of the headform and embedded gage. The cutaway drawing of the headform is used to illustrate the placement of the gage.

A soft-tissue headform with a brain tissue surrogate that is instrumented with an embodiment of the gage described above can be calibrated to determine surrogate-specific deformation-related thresholds for TBI through a combination of experimental and computational investigations, which will require comparisons to clinical head injury data. These calibrated thresholds would need to be based on physiological outcomes through the measurement of injury-relevant parameters, such as internal strain within the headform, rather than rigid body acceleration. The gage described in this document would be able to provide the deformation-based injury metric required for an innovative injury evaluation and helmet certification standard, differing markedly from the contemporary basis of helmet certification. An example of the procedure that could be used for an updated helmet evaluation methodology could involve a drop tower test in which an ATD headform (i.e., the test specimen) is fitted with a helmet to investigate the deformation pattern within the brain surrogate resulting from an impact (FIG. 4). This could be useful in assessing helmet effectiveness as a means of certifying helmets. The deformation-based metric that the instrumented headform would provide is in tune with the contemporary understanding of the linkage between internal strain and TRI.

Torso Impact—Behind Armor Blunt Trauma

Figure 9:
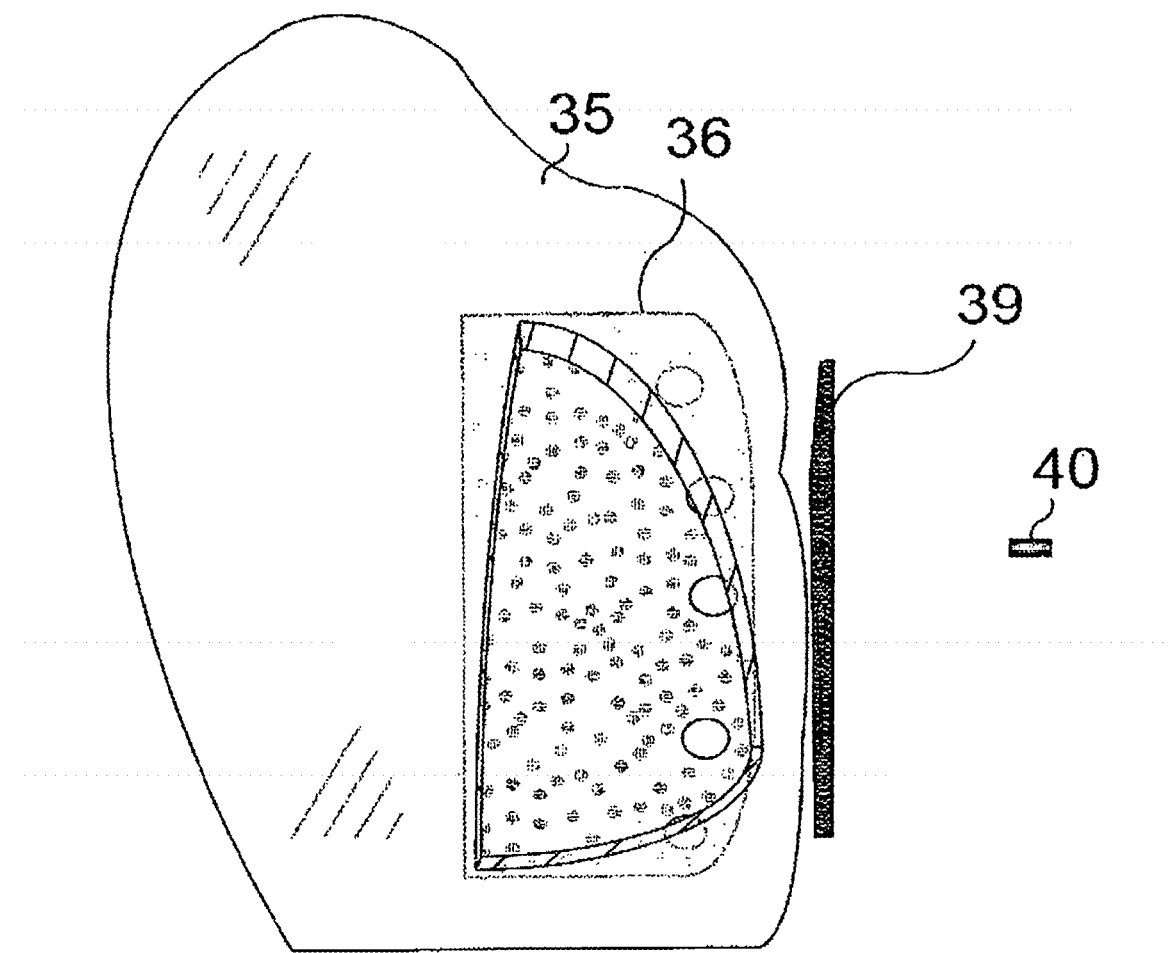
FIG. 9 shows the integration of a scaffolding gage embodiment (of the type shown in FIG. 8) into a soft-tissue simulating torso ATD that can be used to evaluate blunt trauma associated with an impact (e.g., behind armor blunt trauma from a ballistic impact). A cutaway of the torso ATD is shown to illustrate the placement of the internal gage.

The state of the art in determining the injuries related to behind armor blunt trauma involves measurements that are not directly related to the dynamic deformation seen within the body. The gage that is described in the present document is able to provide a direct measure of the deformation within a tissue simulating ATD, a measurement that will provide a superior comparison to the injuries seen during blunt impact events. An example of a blunt impact load applied to the torso resulting from a bullet 40 impacting an armor plate 39 is shown in FIG. 9, illustrating a schematic approach to the type of gauge placement and usage within a torso ATD that could be implemented to investigate the blunt trauma injury from an impact event. This instrumented ATD would need to be placed between the x-ray source 10 and detectors 13 in the same manner as shown schematically in FIG. 1.

What is claimed is:

1. A diagnostic gage device involving a plurality of radiopaque markers enabling a full-field, time-resolved measurement of dynamic deformation and strain within an internal plane of a specimen using x-ray visualization equipment for the purpose of predicting, evaluating or preventing a traumatic biomechanical injury.

2. The see device according to claim 1, further comprising an x-ray contrast agent that is deposited onto or within a substrate or matrix material layer that is mechanically similar, having density and/or elastic Young's modulus not to exceed double the value of these same properties in material constituents of said specimen, in a manner that creates a plurality of high contrast markers as seen in an x-ray image, whereby said markers and substrate are mechanically coupled to said specimen.

3. The gage device according to claim 2, wherein the x-ray contrast agent further comprises any single or multitude of materials or coating comprising, at a minimum, one chemical element with an atomic number higher than the atomic number of each of the chemical elements within the materials used to create said specimen.

4. The gage device according to claim 1, wherein the specimen further comprises an anthropomorphic surrogate model of a biological system, body or body part that are used to predict, evaluate or prevent a biomechanical injury.

5. The gage device according to claim 1, wherein the specimen further comprises any one or combination of a multitude of protective barriers, such as a helmet or external padding that are designed to protect the specimen from trauma.

6. The gage device according to claim 5, wherein the trauma further comprises a direct impact to the specimen, both in a protected or unprotected embodiment, or the result of shock wave, blast wave or other dynamic or static pressure loading of the specimen.

7. The gage device according to claim 5, wherein the trauma further comprises a rapid acceleration or deceleration of the specimen.

8. The gage device according to claim 1, wherein the x-ray visualization equipment further comprises a single or multitude of x-ray sources that are in continuous, discrete or multi-anode source configurations as well as a single or multitude of x-ray digital or analog detectors, fluoroscopes, or film that are used to record the relative movement of the x-ray contras agent markers.

9. The gage device according to claim 1, wherein the x-ray visualization equipment further comprises an arrangement in a single line of sight or stereoscopic orientation that would enable the visualization of the x-ray contrast agents in a planar or in complex curved planes and other three-dimensional orientations respectively.

10. The gage device according to claim 2, wherein the x-ray contrast agent is introduced into said specimen as a series of discrete particles or powder grains, wherein the contrast agent is placed onto or within a substrate or matrix layer that are integrated into the specimen, onto or within an internal or external surface of the specimen itself or within the general volume of the specimen or any combination thereof that produces a plurality of contrasting speckles or markers in an x-ray image that result from a large local presence or local absence of x-ray contrast agent in sufficient concentrations to provide a means of measuring the relative motion of said markers and thus deformation and strain of the specimen.

11. The gage device according to claim 2, wherein the x-ray contrast agent is introduced into said specimen through a deposition or selective coating process onto a substrate or matrix layer that is integrated into the specimen, onto an internal or external surface of the specimen itself or any combination thereof that produces a plurality of contrasting speckles or markers in an x-ray image that result from a large local presence or local absence of x-ray contrast agent in sufficient concentrations to provide a means of measuring the relative motion of said markers and thus deformation and strain of the specimen.

12. A diagnostic gage device involving a plurality of radiopaque markers enabling a full-field, time-resolved measurement of dynamic deformation and strain within an internal plane of a specimen using x-ray visualization equipment for the purpose of material property characterization.

* * * * *